United States Patent [19]
Cianci et al.

[11] Patent Number: 4,512,770
[45] Date of Patent: Apr. 23, 1985

[54] LIQUID DRAINAGE SYSTEM WITH ANTI-REFLUX VALVE

[75] Inventors: James P. Cianci, Cary; Terry N. Layton, Arlington Heights, both of Ill.

[73] Assignee: The Kendall Company, Boston, Mass.

[21] Appl. No.: 461,350

[22] Filed: Jan. 27, 1983

[51] Int. Cl.³ .............................................. A61M 1/00
[52] U.S. Cl. .................................... 604/323; 604/335; 604/350; 137/38; 137/855
[58] Field of Search ................... 128/760, 766, 767; 137/38, 855, 858; 604/317, 323–325, 335, 350

[56] References Cited

U.S. PATENT DOCUMENTS 3,586,041  6/1971  Monestae ............................. 604/323
3,965,900  6/1976  Boedecker ........................... 604/323
4,059,124 11/1977  Hill ....................................... 137/38

FOREIGN PATENT DOCUMENTS 84520  3/1977  Australia ............................... 604/324

Primary Examiner—C. Fred Rosenbaum
Assistant Examiner—J. L. Kruter
Attorney, Agent, or Firm—Powell L. Sprunger

[57] ABSTRACT

A liquid drainage system comprising, a receptacle having a chamber to receive and collect the liquid. The system has a drip chamber having a vent with a bacteria filter covering the vent, and an annular wall having a lower edge defining a valve seat, with the seat being disposed at an acute angle relative to the horizontal when the receptacle is in an upright position. The system has an anti-reflux valve comprising a sheet of flexible material extending across the drip chamber such that the sheet is sufficiently large to engage against the seat peripherally around the drip chamber. The system has a device for retaining an upper portion of the valve against an upper portion of the seat, such that a lower portion of the valve flexes away from the seat when the receptacle is placed in an upright position, and the lower portion of the valve flexes against the seat when the receptacle is disposed in a horizontal position.

7 Claims, 4 Drawing Figures

LIQUID DRAINAGE SYSTEM WITH ANTI-REFLUX VALVE

BACKGROUND OF THE INVENTION

The present invention relates to liquid drainage systems, and more particularly to systems for collection of urine.

Urine drainage systems have been known in the past. Such systems normally comprise a catheter, a drainage receptacle, and a drainage tube communicating between the catheter and receptacle. A distal end of the catheter is passed through the urethra of a patient until the catheter distal end is located in the bladder. Urine then drains through the catheter and drainage tube to the receptacle for collection therein.

It has been discovered that bacteria often accumulates in the collected urine. Hence, it is desirable to prevent the reflux of contaminated urine from the receptacle into the bladder where it might have a deleterious result to the patient. Hence, anti-reflux valves have been provided on the receptacle to prevent the reflux of urine from the receptacle when the receptacle is mishandled, such as when the receptacle is squeezed or placed on its back. However, the prior valves of this sort have required back flow of urine from the receptacle against the valve in order to actuate and close the valve when the receptacle is mishandled.

SUMMARY OF THE INVENTION

A principal feature of the present invention is the provision of an improved liquid drainage system of simplified construction.

The drainage system of the present invention comprises a receptacle having a chamber to receive and collect the liquid. The system has a drip chamber having a vent with a bacteria filter covering the vent, and an annular wall having a lower edge defining a valve seat, with the seat being disposed at an acute angle relative to the horizontal when the receptacle is in an upright position. The system has an anti-reflux valve comprising a sheet of flexible material extending across the drip chamber such that the sheet is sufficiently large to engage against the seat peripherally around the drip chamber. The system has means for retaining an upper portion of the valve against an upper portion of the seat.

A feature of the present invention is that a lower portion of the valve flexes away from the seat when the receptacle is placed in an upright position in order to permit the free flow of liquid therethrough.

Another feature of the invention is that a lower portion of the valve flexes against the seat when the receptacle is disposed in a horizontal position.

Thus, a feature of the present invention is that the valve automatically closes when the receptacle is mishandled by placing it in a horizontal position.

Yet another feature of the invention is that the valve does not require the back flow of liquid to close the valve when the receptacle is mishandled by placing it in a horizontal position.

Further features will become more fully apparent in the following description of the embodiments of the invention and from the appended claims.

DESCRIPTION OF THE PREFERRED EMBODIMENTS

Figure 1:
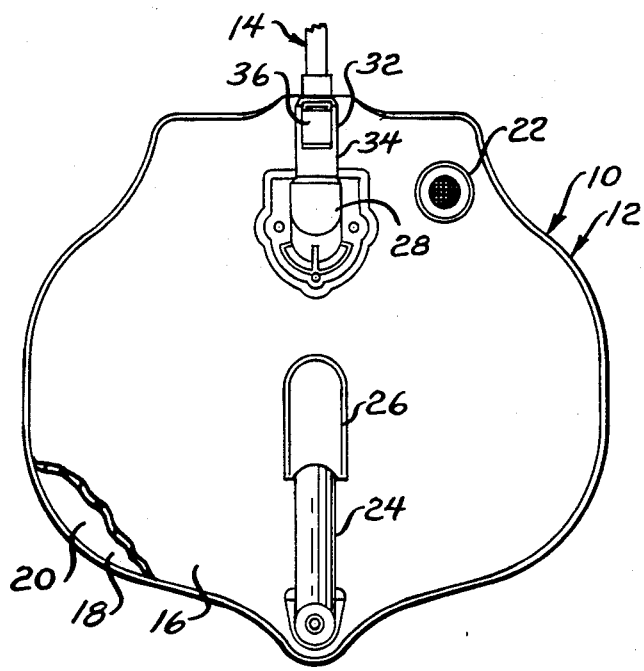
FIG. 1 is a fragmentary elevational view of a liquid drainage system of the present invention.

Referring now to FIG. 1, there is shown a liquid drainage system generally designated 10 comprising a receptacle 12 and a drainage tube 14. In use of the system 10, an upstream end of the drainage tube 14 is connected to the proximal end of a catheter (not shown), and urine drains from the bladder through the catheter and drainage tube 14 into the receptacle 12 for collection therein.

Figure 2:
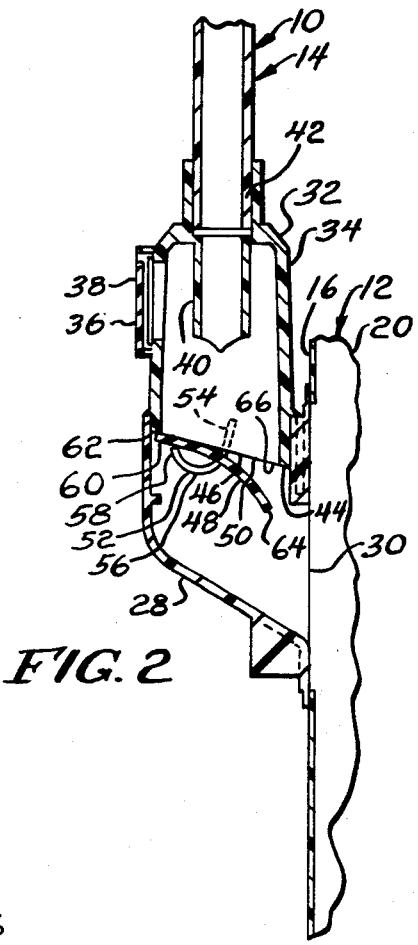
FIG. 2 is a fragmentary sectional view illustrating an anti-reflux valve in an open position when the receptacle is placed in an upright position.

The receptacle has a front wall 16 of flexible plastic material, and a back wall 18 of flexible plastic material joined at their periphery in order to define a chamber 20 intermediate the front wall 16 and back wall 18. The receptacle 12 may have a vent 22 having a bacteria filter of known type in order to permit passage of air from the atmosphere into the chamber 20 while filtering bacteria from the air. As shown, the receptacle 12 may have a lower tubular section 24 having an outer end received in a pocket 26. The tubular section 24 is removed from the pocket 26 in order to drain urine from the receptacle 12, and after drainage of the urine from the receptacle 12 has been completed, the tubular section 24 is again placed in a storage position in the pocket 26. With reference to FIGS. 1 and 2, the receptacle 12 has a hollow connector 28 secured to the front wall 26 of the receptacle 12, with the connector 28 communicating with the chamber 20 through an opening 30 in the front wall 16.

The drainage system 10 has a drip chamber 32 comprising an annular wall 34, with a lower portion of the drip chamber 32 being received in and secured to the connector 28. The drip chamber 32 has an upper vent 36 with a bacteria filter 38 of known type to filter bacteria from the air passing into the drip chamber 32 from the atmosphere. The drip chamber 32 has a drip tube 40 extending into the drip chamber 32 and spaced from the wall 34 in order to define an air break for the urine passing through the drip tube 40 into the drip chamber 32, and prevent a liquid path at the central portion of the drip chamber 32 for retrograde bacteria migration from the receptacle 12 back to the drainage tube 14. As shown, a downstream end 42 of the drainage tube 14 is received in an upper portion of the drip chamber 32, such that the drainage tube 14 communicates with the drip chamber 32.

Figure 3:
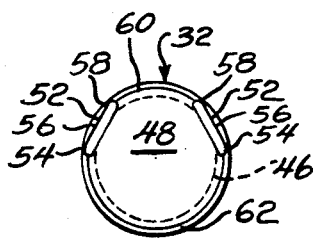
FIG. 3 is a detail view illustrating the underside of the anti-reflux valve.

With reference to FIGS. 2 and 3, the wall 34 has an annular lower edge 44 defining a valve seat 46. As shown, the seat 46 is disposed at an acute angle relative to the horizontal when the receptacle 12 and drip chamber 32 are placed in an upright position. In a preferred form, the seat 46 is disposed at an angle in the range of 15 to 60 degrees to the horizontal when the receptacle 12 and drip chamber 32 are disposed in an upright or vertical position.

The system 10 has an anti-reflux valve 48 comprising a sheet of flexible material, such as rubber or silicone rubber, extending across an opening 50 defined by the edge 44 of the drip chamber 32, such that the circular sheet is sufficiently large to engage against the seat 46 peripherally around the drip chamber 32. As shown, the valve 48 has a pair of opposed retaining arms 52 having one end 54 secured in a central portion of the drip chamber 32 and extending through openings in a central portion of the valve 48. The arms 52 have an arcuate portion 56 with the other ends 58 of the arms 52 engaging against an upper portion 60 of the valve 48 on the underside thereof and holding it against an upper portion 62 of the seat 46. In this configuration, a lower portion 64 of the valve 48 is free to flex away from a lower portion 66 of the seat 46. In a preferred form, as shown, the lower portion 64 of the valve 48 and the lower portion 66 of the seat 46 are located nearest the receptacle 12, and the upper portion 60 of the valve 48 and the upper portion 62 of the seat 46 are located furthest away from the receptacle 12.

In use, with reference to FIG. 2, when the receptacle 12 and drip chamber 32 are placed in a vertical position, the lower portion 64 of the valve 48 automatically flexes away from the lower portion 66 of the seat 46 resulting from the action of gravity on the weight of the valve 48. Thus, the valve 48 automatically opens to permit passage of urine through the drip chamber 32 and connector 28 when the receptacle 12 and drip chamber 32 are placed in an upright position. The flow of urine through the valve 48 is facilitated by the vent 36 which prevents accumulation of urine in the drip chamber 32.

Figure 4:
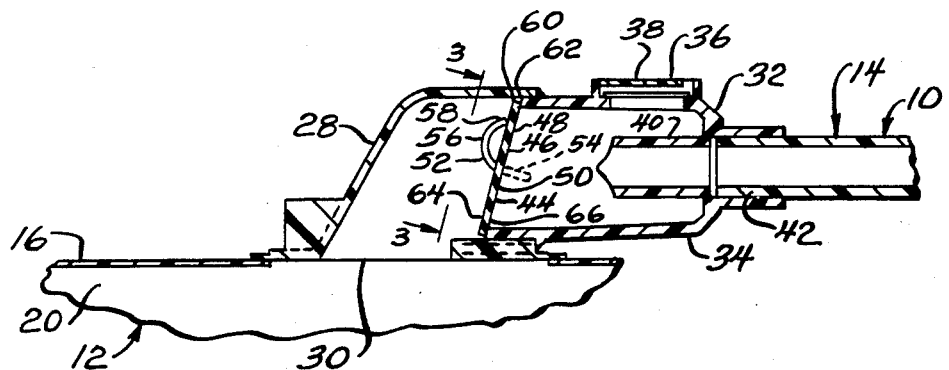
FIG. 4 is a fragmentary sectional view illustrating the anti-reflux valve in a closed position when the receptacle is placed in a horizontal position.

With reference to FIG. 4, when the receptacle 12 is mishandled by placing the receptacle 12 on its back, the lower portion 64 of the valve 48 automatically flexes against and sealingly engages against the lower portion 66 of the seat 46 due to the action of gravity on the weight of the valve 48. Thus, the valve 48 automatically assumes its closed configuration when the receptacle 12 is placed on its back, and it is necessary to require the force of refluxing urine against the valve 48 in order to close the valve 48. Accordingly, the valve 48 of the present invention is more responsive in its closure to prevent the reflux of urine from the receptacle 12 into the bladder which otherwise might cause possible deleterious results to the patient.

The foregoing detailed description is given for clearness of understanding only, and no unnecessary limitations should be understood therefrom, as modifications will be obvious to those skilled in the art.

We claim:

1. A urine drainage system, comprising:
a receptacle having a chamber to receive and collect urine;
a drip chamber in fluid communication with the chamber receptacle and having an annular wall with a lower, open peripheral edge defining a valve seat, said seat being disposed at an acute angle relative to a horizontal plane when the receptacle is in an upright position and thus defining an upper seat portion and a lower seat portion;
an anti-reflux valve comprising a sheet of flexible material extending over said valve seat, said anti-reflux valve sheet being of sufficiently large dimensions to entirely cover said valve seat, said valve having an upper valve portion, underline and a lower valve portion; and
means for retaining said upper valve portion against said upper seat portion and said anti-reflux valve being made of flexible material, such that said lower valve portion flexes away from the lower seat portion when the receptacle is placed in an upright position, and said lower valve portion flexes against the lower seat portion when the receptacle is disposed in a horizontal portion, the retaining means comprising a pair of opposed arcuate retaining arms, each arm having one end secured in a central portion of the drip chamber and extending through central portions of said valve seat and said valve, the arm terminating in an arcuate end engaging against said upper valve portion on the underside thereof and holding it against said upper seat portion.

2. The system of claim 1 including a connector attached to a wall of the receptacle and communicating with the chamber, and in which a lower portion of the drip chamber is received in the connector.

3. The system of claim 1 including a drip tube extending into the drip chamber and being spaced from the wall of the drip chamber.

4. The system of claim 1 wherein said lower seat portion is located nearest the receptacle, and in which said upper seat portion is located farthest from the receptacle.

5. The system of claim 1 wherein the seat is disposed at an angle in the range of 15 to 60 degrees relative to the horizontal when the receptacle is placed in an upright position.

6. The system of claim 1 wherein the drip chamber has a vent with a bacteria filter covering the vent.

7. A urine drainage system, comprising:
a receptacle having a chamber to receive and collect urine, and a connector attached to a wall of the receptacle and communicating with the chamber;
a drip chamber having a lower portion received in the connector, said drip chamber having a vent with a bacteria filter covering the vent, and an annular wall with a lower, open peripheral edge defining a valve seat, said seat being disposed at an acute angle relative to a horizontal plane when the receptacle is in an upright position, and thus defining a lower seat portion which is located nearest the receptacle and an upper seat portion which is located farthest from the receptacle;
an anti-reflux valve comprising a sheet of flexible material extending over said valve seat, said anti-reflux valve sheet being of sufficiently large dimensions to entirely cover said valve seat, said valve having an upper valve portion, underside and a lower valve portion; and
means for retaining said upper valve portion against said upper seat portion comprising a pair of opposed arcuate retaining arms, each arm having one end secured in a central portion of the drip chamber and extending through central portions of said valve seat and said valve, the arm terminating in an arcuate end engaging against said upper valve portion on the underside thereof and holding it against said upper seat portion.

* * * * *